United States Patent [19]
Rand et al.

[11] Patent Number: 4,644,168
[45] Date of Patent: Feb. 17, 1987

[54] ELECTRON BEAM DEFLECTING MAGNET ASSEMBLY FOR A SCANNING ELECTRON BEAM COMPUTED TOMOGRAPHY SCANNER

[75] Inventors: Roy E. Rand; Dan Y. Wang, both of Palo Alto, Calif.

[73] Assignee: Imatron Inc., So. San Francisco, Calif.

[21] Appl. No.: 610,102

[22] Filed: May 14, 1984

[51] Int. Cl.⁴ ............................................. H01J 3/34
[52] U.S. Cl. .............................. 250/398; 250/396 ML
[58] Field of Search ........... 250/396 R, 396 ML, 398; 335/210, 213, 214; 378/137

[56] References Cited

U.S. PATENT DOCUMENTS

| | | | |
|---|---|---|---|
| 3,007,087 | 10/1961 | Corpew | 335/213 |
| 3,430,169 | 2/1969 | Gabor | 335/213 |
| 3,731,241 | 5/1973 | Coupland | 335/213 |
| 3,911,321 | 10/1975 | Wardly | 250/396 ML |
| 4,122,346 | 10/1978 | Enge | 250/396 ML |
| 4,352,021 | 9/1982 | Boyd et al. | 378/137 |

OTHER PUBLICATIONS

Mills et al., "A Flux Theorem for the Design of Magnet Coil Ends," Particle Accelerators, vol. 5, pp. 227-235 (1973).

*Primary Examiner*—Bruce C. Anderson
*Assistant Examiner*—Paul A. Guss
*Attorney, Agent, or Firm*—Flehr, Hohbach, Test, Albritton & Herbert

[57] ABSTRACT

A deflecting magnet assembly for scanning an incident beam of charged particles in a scanning electron beam computed tomography scanner. The configuration (including angular orientation and coil end connection geometry) of the coils which comprise the magnet is selected to approximate the field of a pure dipole. In addition, a magnetic shield is used which equalizes the effective radii of the constituent coils and thereby simplifies construction of the assembly.

10 Claims, 10 Drawing Figures

ELECTRON BEAM DEFLECTING MAGNET ASSEMBLY FOR A SCANNING ELECTRON BEAM COMPUTED TOMOGRAPHY SCANNER

The present invention relates to electron beam apparatus and techniques which are suitable for producing X-rays in a tomographic X-ray transmission system of the type disclosed in U.S. Pat. No. 4,352,021, filed Jan. 7, 1980, in the name of BOYD ET AL and to an improvement of an electron beam control assembly for such a scanning system which assembly is of the type introduced in co-pending U.S. patent application, Ser. No. 434,252, filed Oct. 14, 1982, in the name of RAND. The Boyd et al patent and the Rand application are hereby incorporated by reference. The present invention also relates to a deflecting magnet assembly and its associated function in scanning an electron beam relative to an X-ray target. In particular, the rotating magnetic field of the deflecting magnet closely approximates a pure dipole field in its constant magnitude and direction at any given time.

Figure 1:
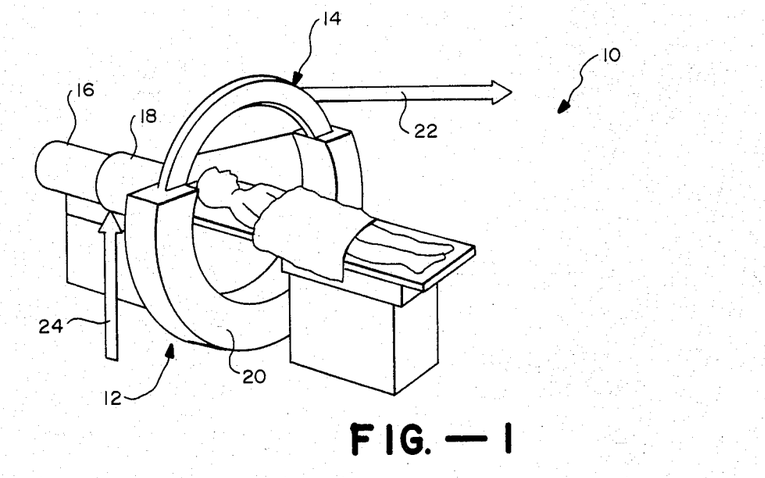
FIG. 1 is a schematic diagram in perspective showing a computed tomography X-ray transmission scanning system which utilizes an assembly for producing and controlling an electron beam within an evacuated beam chamber.
Figure 2:
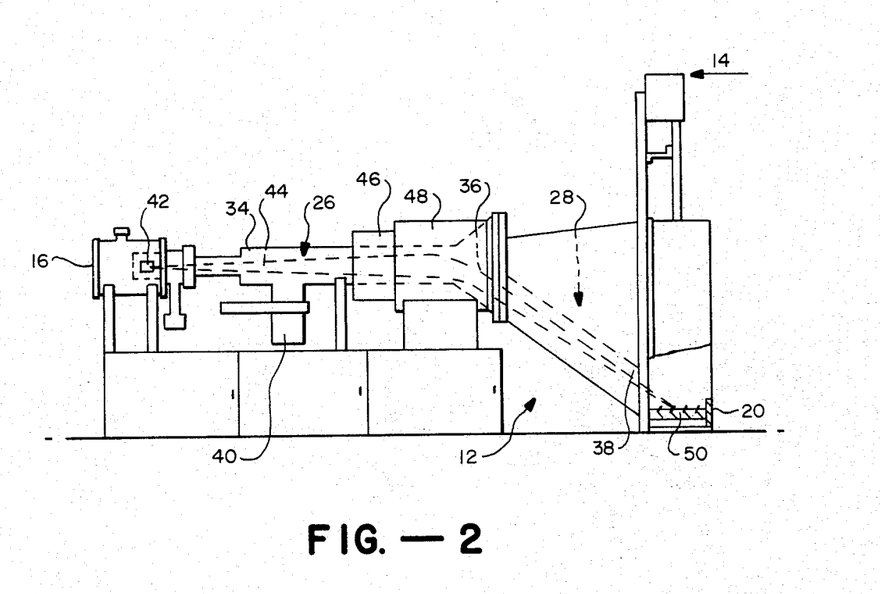
FIG. 2 is a cross-sectional view of the system shown in FIG. 1.

FIG. 1 of the drawings is a schematic representation of a computed tomographic X-ray transmission scanning system 10 of the type treated in the Boyd et al patent and thus needs only brief discussion here. The system 10 is divided into three major functional components: an electron beam production and control assembly 12, detector array 14 and a data acquisition and computer processing component (not shown) which does not relate to the present invention. Referring also to FIG. 2, the present invention is primarily concerned with the apparatus and functioning of the electron beam production and control assembly 12. This assembly includes a housing 26 which defines an elongated, vacuum sealed chamber 28 extending between rearward end 16 and forward end 20 of the system. The housing is divided into three co-axial sections: a rearwardmost chamber section 34, an intermediate control section 36 and a forwardmost section 38. The overall chamber is evacuated of internal gases by means such as a conventional vacuum pump indicated generally at 40. Electron gun 42 is located proximate the rearward end 16 in chamber section 34 for producing a continuously expanding electron beam 44 and for directing the beam through chamber section 34 to control chamber 36. The intermediate control chamber section 36 bends the electron beam 44 through the forward section 38 of the assembly in a scanning manner and focuses it onto a cooperating arrangement of targets 50 for the purpose of generating X-rays. In particular, control chamber section 36 includes focusing coils 46 and deflecting coils 48 which bend the incoming beam from section 34 into forwardmost chamber section 38. At the same time, the coils focus the beam to a beam spot which is intercepted at the X-ray targets 50 located at the forward end 20 of the chamber section 38. The X-rays produced are detected by the detector array 14 for producing resultant output data which is applied to the computer processing arrangement as indicated by the arrow 22, FIG. 1, for processing and recording the data. The computer arrangement also includes means for controlling the electron beam production and control assembly 12 as indicated by arrow 24, FIG. 1.

The field of use of the electron beam and the system 10—medical diagnosis—and the fact that the diagnostic data which is derived from the X-rays is extremely sensitive to aberrations of the electron beam optics and is susceptible to any system error, make it highly desirable to eliminate any deviation whatsoever from ideal electron beam optics. The requirement of near-perfection in the system beam optics in turn dictates that the magnetic field of the deflecting coil approximate as closely as possible a pure dipole field. Because of the desirability of this goal it is one object of the present invention to provide a deflecting magnet which has acceptably small non-uniformities in the magnitude and direction of its magnetic field at any given time and as a result produces a very high quality scanned beam spot.

It is a parallel object to provide a deflecting magnet assembly for scanning an electron beam incident thereto about a target and which deflects the beam of electrons and allows rotation of the plane of deflection about the magnet axis to thereby controllably scan the electron beam.

It is still another object of the present invention to provide a deflecting magnet assembly of the type described above in which the magnetic field is uniform across any plane normal to its axis and whose direction is in this plane and is constant in space and can be made to rotate with time about the axis.

These and other objects are provided in a deflecting magnet in the form of a magnetic coil assembly which is configured to provide a field magnitude and a direction which substantially approximate those of a pure dipole field.

Figure 3:
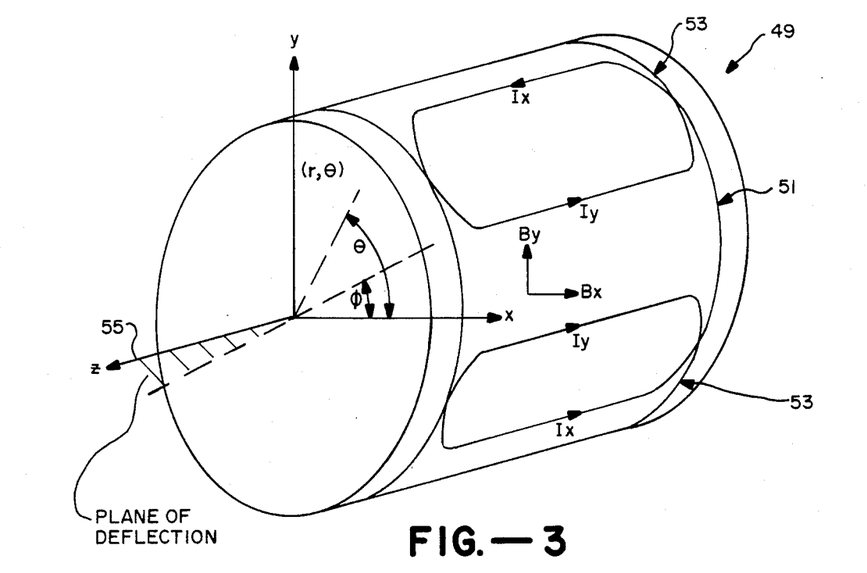
FIG. 3 schematically illustrates the general configurational and geometrical relationships of the improved magnetic coil of the present invention.
Figure 4:
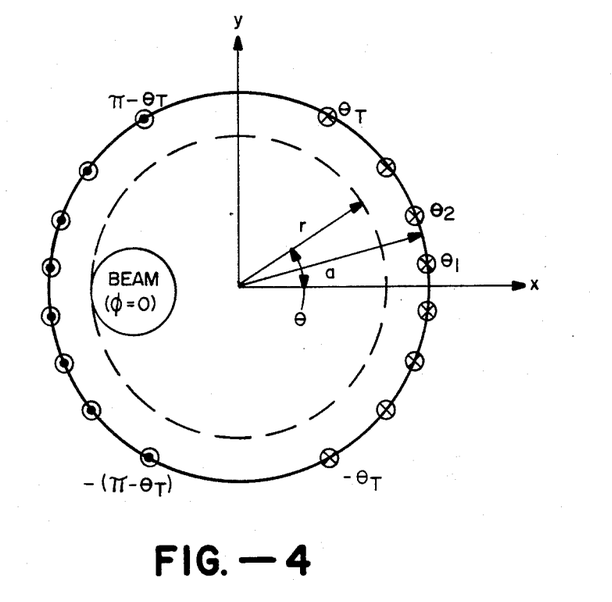
FIG. 4 schematically illustrates a cross-section perpendicular to the axis of the magnetic coil of FIG. 3, showing the coil for which the plane of deflection is at $\phi=0$ (y-coil)

In particular, the number of turns of the coils used in the assembly, the coil radii, and the angular positions of the turns and the coil end connections are configured to closely approximate a field magnitude $$|B| = \sqrt{B_x^2 + B_y^2} = B_o, \tag{1}$$

which is constant everywhere in a cylinder which contains the beam, independent of the coordinates r, $\theta$ and $\phi$, and the field direction $$B_x/B_y = -\tan \phi, \tag{2}$$

which is independent of r and $\theta$. (The coordinate system and r, $\theta$ and $\phi$ are defined elsewhere, including in FIGS. 3 and 4.)

In a particular working embodiment of the deflecting magnet, the total number of coil turns and the angular position and spacing of each turn thereof are selected to satisfy specific tolerances defined by error formulae for the constancy of the non-rotating magnetic field of each coil and for the constancy of the rotating field in the plane of deflection.

In still another aspect, the deflecting magnet includes a magnetic shield which functions to increase and confine the field due to the windings, to shield the region inside the magnet from external magnetic fields, and also to equalize the effective radii of the x and y coil windings. The equalization function of the shield compensates for different physical radii $a_x$ and $a_y$ of the x and y coil windings and thereby permits a simplified coil construction employing different physical radii. These and other aspects of the invention will be discussed in more detail in conjunction with the drawings wherein:

Figure 7:
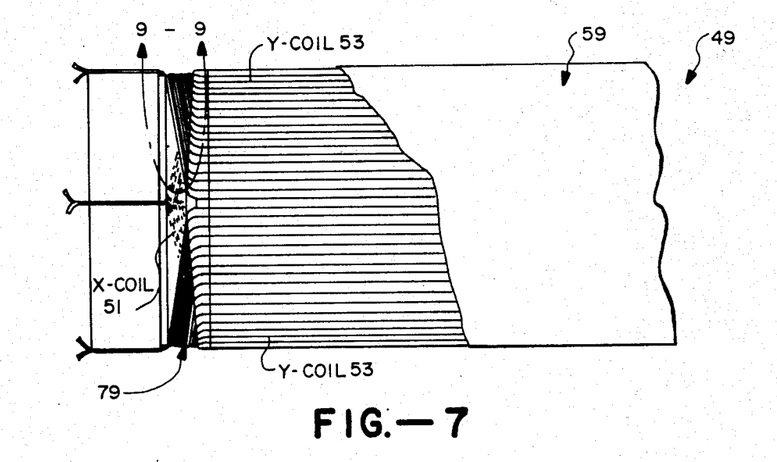
FIGS. 7 and 8 are, respectively, partial plan and partial cross-section views of a magnetic coil assembly which incorporates aspects of the present invention.
Figure 8:
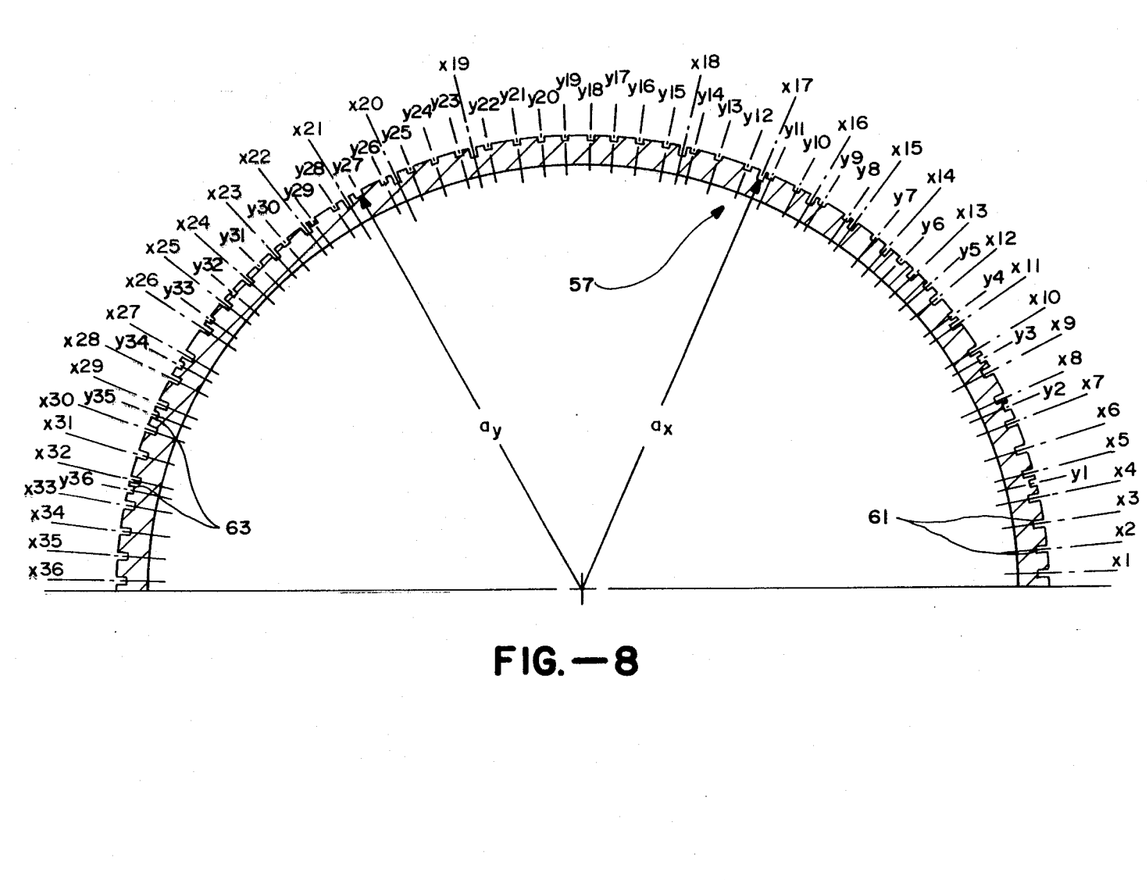

A diagrammatic illustration of an actual working example of a coil magnet assembly 49 which embodies the features of the present invention is shown in partial plan view in FIG. 7 and in cross-section in FIG. 8. While the invention is described relative to its use in a computed tomography scanner, it is applicable in general to deflecting magnets and to the function of scanning a beam of charged particles. The desired magnetic field magnitude and directional properties are provided by the particular configuration of magnet assembly 49, specifically the angular distribution $\theta_t$ of the wire turns, t, and the value of the total number of turns, T; the configuration of the end connections between the axially-extending sections of each wire turn, for example, the end connections between axial coil sections at $\theta_t$ and $\pi-\theta_t$ and between $-\theta_t$ and $-(\pi-\theta_t)$ (see FIG. 4); and by equalization of the effective physical radii of the different coils. In addition, a shield 59 of very high permeability shields the region inside the magnet from external magnetic fields and increases and confines the field due to the windings.

The magnetic shield design and construction also provide the desired equalization of the coil radii.

Before considering specific constructional details of the magnet assembly 49 and in order to better understand its design, it is helpful to review and understand the theory incorporated in the physical coil configurations. The theory of the overall system 10 is described at length in the co-pending Rand U.S. patent application and need not be repeated here. In the main then, the theory treated here is specific to the deflecting magnet design.

Referring specifically to FIG. 3, there is shown a highly schematized illustration of magnetic coil assembly such as the assembly 49 which is useful in considering the aspects of a pure dipole field. The magnetic coil assembly is defined with reference to arbitrarily designated mutually orthogonal coordinate axes x, y, z. For simplicity, one coil turn is shown from each of one of the continuous x-coils 51 and two continuous y-coils 53—53. The coil turns comprise axial sections which extend substantially parallel to the z-axis and end connections which interconnect the two axial sections of each coil turn. The cross-sectional planes of each coil lie within planes parallel to the xy plane and the location of the radius therein is defined by polar coordinates (r, $\theta$).

The plane of deflection of the magnetic field is the plane perpendicular to the magnetic field direction. The plane of deflection is defined by $\phi$ and the z-axis (cylinder axis 55), where $\phi$ is the angle between the x-axis and the plane of deflection. (For example, in FIG. 4, the x-axis is in the plane of deflection; $\phi=0$.). With these defined relationships, electric currents $I_x$ and $I_y$ in the respective coils will produce magnetic fields $B_x$ and $B_y$ respectively. If the angle $\phi$ and the z-axis define the plane of deflection, then currents $I_x=-I_o\sin\phi$, $I_y=I_o\cos\phi$ will produce fields $B_x=-B_o\sin\phi$, $B_yB_o\cos\phi$ where ideally the resultant field, $\vec{B}=\vec{B}_x+\vec{B}_y$ is a pure dipole field inside the volume of the finite-cylinder magnet and zero outside. That is, the field magnitude $$|B| = \sqrt{B_x^2 + B_y^2} = B_o \tag{1}$$

is constant everywhere inside the cylinder, independent of r, $\theta$, z and $\phi$ and the field direction $$B_x/B_y = -\tan\phi \tag{2}$$

is independent of r, $\theta$ and z. (Strictly, the confining volume need not be cylindrical.)

Since the beam is initially centered on the z-axis and remains close to the plane of deflection, and taking symmetry into account, to achieve the desired constancy in field magnitude, it is sufficient to ensure that $B_o$ is independent of r, $\theta$ and $\phi$. That is, variation of $B_o$ with z is not important. In practice, a variation of $B_o$ by no more than 0.2% across the portion traversed by the beam of any cross-section of the magnet is acceptable. Thus, the approximation of a pure dipole field in magnetic coil assembly 49 requires that the conditions associated with equations (1) and (2) be satisfied only in every cross-sectional plane and to an accuracy of 0.2%.

As developed below, in one aspect of the present invention, the angular positions $\theta_t$ of the axial coil sections are chosen so that the magnetic coil assembly closely approximates the ideals expressed in equations (1) and (2), to the particular required accuracy or tolerance of 0.2%. The required accuracy of 0.2% is obtained if neither of the following root mean square (RMS) errors (associated, respectively, with the non-rotating magnetic field in the plane of FIG. 4 and the rotating field in the plane of deflection) exceeds 0.2% of the value of the magnetic field on the magnet axis 55 (FIG. 3). The RMS error associated with the non-rotating case is (a) the RMS deviation of the magnetic field in any transverse plane, from its value on-axis, averaged over all polar angles ($\theta$) and over all radii (r') up to a specified radius (r) for each pair of coils separately, whereas the RMS error associated with the rotating case is (b) the RMS deviation in any transverse plane, of the magnetic field in the plane of deflection from its value on-axis, averaged over all values of the angle ($\theta$) defining the plane of deflection and over all radii (r') up to a specified radius (r) for the two pairs of coils acting together.

Of course, the tolerance of 0.2% and the specified maximum radius r may be different in other applications.

As a starting point, the requirement on field uniformity is most severe where the electron beam leaves the magnetic field of the deflecting magnet assembly 49. This situation is represented by FIG. 4 where it is assumed that $\phi=0$. A convenient quantitative measure of the non-uniformity of the non-rotating magnetic field in the plane of FIG. 4 is provided by the RMS error related to (a) above, viz:

$$\text{Error}_1 (r/a) = \quad (3)$$

$$\sqrt{\frac{1}{2\pi r/a} \int_0^{r/a} \int_0^{2\pi} \left(\frac{B - B_o}{B_o}\right)^2 d\theta dr'}\bigg|_{\phi=0}$$

where a is the radius of the coil; B is the value of the magnetic field at (r', $\theta$); $B_o$ is its value at the origin; and r is the maximum polar radius to which the beam extends.

It is sufficient that this error be less than 0.2%, for the average variation of the field over the beam path will then be on the order of 0.1% and since most of the deflection of the beam occurs at smaller radii, the deflections of individual electrons will certainly vary by less than 0.1%.

A similar measure of the variation of the field in the plane of deflection, as the angle $\phi$ rotates, is provided by the associated RMS error related to (b) above, viz:

$$\text{Error}_2 (r/a) = \quad (4)$$

$$\sqrt{\frac{1}{2\pi r/a} \int_0^{r/a} \int_0^{2\pi} \left(\frac{B - B_o}{B_o}\right)^2 d\phi dr'}\bigg|_{\phi=\theta}$$

Again, this quantity must be less than 0.2%.

The quantities represented by error formulae (3) and (4) are conveniently evaluated using the approximation of an infinitely long deflecting magnet, i.e., without considering end effects. Considering first the error formula (3) for the uniformity of a non-rotating field, for $\phi=0$, it is expedient to describe the magnetic field as a multipole expansion $$B_y = -\sum_{n=1}^{\infty} S_n \left(\frac{r}{a}\right)^{n-1} \cos(n-1)\theta, \, n = 1,3,5 \ldots \quad (5)$$

where the 2n-pole component of the field is given by $$S_n = \frac{8I_y\eta}{n} \sum_{t=1}^{T} \cos n\theta_t, \quad (6)$$

and $\eta = \frac{1}{4}\pi\epsilon_o c$ is the impedance of free space. (The even multipoles are zero by symmetry.)

Ideally, one requires the dipole contribution (n=1) to be finite ($S_1 \neq 0$) and all other multipoles to be zero. Then $B_y = B_o = S_1 = $ constant.

Using this multipole expansion of the magnetic field, it can then be shown that $$\text{Error}_1 (r/a) = \left[\frac{1}{2} \sum_{n=3,5,7}^{\infty} \frac{S_n^2}{S_1^2} \frac{n^2}{2n-1} \left(\frac{r}{a}\right)^{2n-2}\right]^{\frac{1}{2}} \quad (3')$$

Considering next error formula (4) for the constancy of the rotating field in the plane of deflection, the multipole formula corresponding to equation (3') is $$\text{Error}_2 (r/a) = \left[\frac{1}{2} \sum_{n=3,5,7}^{\infty} \frac{S_n^2}{S_1^2} \frac{n^2}{2n-1} \left(\frac{r}{a}\right)^{2n-2} + \sum_{n=3,7,11}^{\infty} \frac{S_n S_{n+2}}{S_1^2} \frac{n(n+2)}{2n+1} \left(\frac{r}{a}\right)^{2n}\right]^{\frac{1}{2}} \quad (4')$$

For the chosen value of r/a, which is fixed by the beam geometry and for selected values of T, the problem now is to define methods for calculating the values of $\theta_t$ which will give acceptable numerical values for the expressions (3') and (4'). Six different approaches to solving this problem are described below.

(a) Zero Multiple Solution (ZMS)

It is conventional practice (for superconducting particle beam transport magnets for instance) to choose the wire angles so that $S_1 \neq 0$ and $S_n = 0$ for $n = 3, 5, 7, \ldots$ (2T+1). This solution is adequate only if the value of (r/a) is small enough that $(r/a)^{2T+2}$ is negligible for the first non-zero multipole term.

In the scanner system 10 (FIG. 1), it is desirable to make the coil radius a as small as possible for a given coil length and beam path so that as much as possible of the aperture is used. In short, it is desirable for (r/a) to be close to unity (in fact, the value chosen is r/a=0.867). For this value of (r/a), the ZMS solution was found to be inadequate for T<4. For T≤4, no solution of this type could be found. For T=4, the values of $\theta_t$ are $$\theta_t = (\pi/2)(\frac{1}{3} \pm 1/5 \pm 1/7). \quad (7)$$

The other solutions are (b) Equally Spaced Sine Solution (ESSS)

$$\sin \theta_t = \frac{(2t-1)}{2T}, \, t = 1,2,3 \ldots T. \quad (8)$$

(c) Modified Equally Spaced Sine Solution 1 (MESSS1)

$$\sin \theta_t = \delta_1 + \frac{(2t-1)}{2T}, \, t = 1,2,3 \ldots T. \quad (9)$$

where $\delta_1$ is chosen to minimize the magnitude of expression (3').

(d) Modified Equally Spaced Sine Solution 2 (MESSS2)

$$\sin \theta_t = \delta_2 + \frac{(2t-1)}{2T}, \, t = 1,2,3 \ldots T. \quad (10)$$

where $\delta_2$ is chosen to minimize the magnitude of expression (4').

(e) Minimum Non-Rotating Error Solution (MNRES)

In this solution, all values of $\theta_t$ were allowed to vary independently and were chosen by a computer program to minimize the magnitude of expression (3').

(f) Minimum Rotating Error Solution (MRES)

This solution is similar to MNRES solution (e) in approach, but values of $\theta_t$ were chosen to minimize the magnitude of expression (4').

The evaluation of the error expressions (3') and (4') is shown in Table 1 for solutions (a) through (f) for $T=4$ and (b) through (f) for $T=18$. It should be noted that simple estimation of the magnitude of error$_1$ for $r/a=0.867$ showed that T must be at least 16 for the required field uniformity. The evaluation of $T=18$, discussed below, showed that $T=18$ provided the required field uniformity. (There is, of course, a continuum of solutions containing (b), (c) and another containing (e) and (f).) Values of $\theta_t$ are given in Table 2 for each solution with 18 turns.

The results for four turns (Table 1) show that the Zero Multipole Solution is clearly inferior to all other solutions, and this solution was, therefore, pursued no further. Results for 18 turns show that, in all cases, the uniformity of the non-rotating field is most critical. For the present application, 18 turns was selected, since for all solutions the RMS errors are acceptable and less than $2\times 10^{-3}$ (0.2%).

More turns would, of course, be better from the point of view of greater field uniformity, but a secondary consideration was the angular separation of the x and y windings. With the preferred dimensions (radius, $a \simeq 12$ inches) and method of construction, the minimum permitted separation of any pair of x and y turns is 0.62°. (This is a purely mechanical constraint imposed because machining the coil form requires a 0.020 inch minimum separation between the closest part of any two x and y wires. A different method of fabrication could alter this constraint.) For each solution and 18 turns, minimum angular separations are shown in Table 2. This requirement allows only solutions ESSS and MESSS2 to be acceptable in the present application.

TABLE 1

Magnetic Field Non-Uniformity (RMS Errors) For Long Cylindrical Magnets Using Various Solutions for Wire Spacing

| Solution | RMS Error 1 (Non-Rotating) Formula (3') | RMS Error 2 (Rotating) Formula (4') |
|---|---|---|
| 4 Turns | | |
| (a) ZMS | $3.45 \times 10^{-2}$ | $4.61 \times 10^{-2}$ |
| (b) ESSS | $1.95 \times 10^{-2}$ | $1.16 \times 10^{-2}$ |
| (c) MESSS1 | $1.81 \times 10^{-2}$ | $1.09 \times 10^{-2}$ |
| (d) MESSS2 | $1.84 \times 10^{-2}$ | $1.07 \times 10^{-2}$ |
| (e) MNRES | $1.77 \times 10^{-2}$ | $1.21 \times 10^{-2}$ |
| (f) MRES | $2.1 \times 10^{-2}$ | $5.19 \times 10^{-3}$ |
| 18 Turns | | |
| (b) ESSS | $1.61 \times 10^{-3}$ | $4.6 \times 10^{-4}$ |
| (c) MESSS1 | $1.27 \times 10^{-3}$ | $8.4 \times 10^{-4}$ |
| (d) MESSS2 | $1.46 \times 10^{-3}$ | $3.6 \times 10^{-4}$ |
| (e) MNRES | $6.9 \times 10^{-4}$ | $2.3 \times 10^{-4}$ |
| (f) MRES | $7.8 \times 10^{-4}$ | $3.5 \times 10^{-5}$ |

TABLE 2

Wire Positions (Values of $\theta_t$ in Degrees) For The Configurations of TABLE 1: 18 Turns

| t/Solution | ESSS | MESSS1 | MESSS2 | MNRES | MRES |
|---|---|---|---|---|---|
| 1 | 1.592 | 1.477 | 1.557 | 1.570 | 1.570 |
| 2 | 4.780 | 4.665 | 4.746 | 4.768 | 4.848 |
| 3 | 7.984 | 7.868 | 7.949 | 7.932 | 7.920 |
| 4 | 11.212 | 11.095 | 11.177 | 11.143 | 10.933 |
| 5 | 14.478 | 14.359 | 14.442 | 14.436 | 14.493 |
| 6 | 17.792 | 17.671 | 17.755 | 17.630 | 18.023 |
| 7 | 21.168 | 21.046 | 21.132 | 21.100 | 20.994 |
| 8 | 24.624 | 24.498 | 24.587 | 24.495 | 24.250 |
| 9 | 28.179 | 28.049 | 28.140 | 27.900 | 28.063 |
| 10 | 31.855 | 31.721 | 31.815 | 31.893 | 31.734 |
| 11 | 35.685 | 35.544 | 35.643 | 35.172 | 35.541 |
| 12 | 39.709 | 39.560 | 39.664 | 39.767 | 39.546 |
| 13 | 43.983 | 43.824 | 43.935 | 43.382 | 43.611 |
| 14 | 48.590 | 48.417 | 48.538 | 48.517 | 48.230 |
| 15 | 53.664 | 53.471 | 53.606 | 52.977 | 53.405 |
| 16 | 59.442 | 59.217 | 59.374 | 59.210 | 59.133 |
| 17 | 66.444 | 66.158 | 66.358 | 65.391 | 65.368 |
| 18 | 76.464 | 75.983 | 76.318 | 75.927 | 76.268 |
| Minimum Angular Separation | | | | | |
| $\Delta\theta_{15}$ | $-0.651$ | $-0.985$ | $-0.751$ | $-1.851$ | $-1.054$ |
| $\Delta\theta_{16}$ | 1.297 | 0.938 | 1.189 | 1.103 | 0.867 |
| $\Delta\theta_{17}$ | 1.068 | 0.656 | 0.945 | $-0.114$ | $-0.382$ |
| $\Delta\theta_{18}$ | 0.942 | 0.342 | 0.760 | 0.363 | 0.761 |

With more than 18 turns, for the given radial dimensions, no solution was acceptable in the present application. For practical reasons, i.e., to optimize the end connection configuration, ESSS was actually chosen.

To summarize, a class of possible solutions is one in which the angular positions $\theta_t$ of the axial sections 60 of each coil are selected according to $$\sin\theta_t = \frac{2t-1}{2T} + \delta,$$

where $t=1, 2, 3 \ldots T$ (the number of coil turns). The parameter $\delta$ may be chosen as: (1) the value which minimizes the previously-described RMS error in the non-rotating case (for $T=18$, $r/a=0.867$ in the illustrated working embodiment of coil assembly 49); (2) the value which minimizes the previously-described RMS error in the rotating case (again for $T=18$, $r/a=0.867$ in the illustrated working embodiment); or (3) $\delta=0$. Of these, the last two are acceptable. This last value, being the most compact solution of this type, is described in greater detail subsequently. All three of these prescriptions satisfy the particular criteria that both RMS errors be $\leq 0.2\%$.

Of course, depending upon the particular coil parameters (e.g., smaller wire diameter or larger coil diameter), one or more of the other solutions may be applicable exclusive of, or in addition to, the ESSS solution in selecting the values of $\theta_t$. These solutions include a class in which the angular positions $\theta_t$ of the axial sections 60 of each coil are treated as T independent parameters which are varied to minimize the previously-described RMS error for the non-rotating field or the previously-described RMS error for the rotating field.

Referring again to the plan view shown in FIG. 7, and to the partial cross-sectional view thereof shown in FIG. 8, the above theory and ESSS solution were implemented in the magnetic coil assembly 49 of the present invention. The coil assembly comprises a cylindrical coil form 57 (FIG. 8) of dielectric material such as resin-impregnated fiberglass, and an overlying magnetic shield 59 (FIG. 7). The coil form 57 has thirty-six slots 61—61 cut or otherwise formed in the outer surface thereof, individually designated X1-X36, for receiving the axial segments of like designation of a particular x-coil 51. (Only half the coil form is shown.)

Similarly, the form 57 has thirty-six slots 63—63, individually designated Y19-Y54, for receiving the axial segments of a particular y-coil. It should be noted that the coil assembly comprises two, eighteen-turn x-coils 51 and two, eighteen-turn y-coils 53, each of which spans approximately 180° of arc in accordance with the configurational and positional definitions of FIGS. 3 and 4 and the solutions T=18 for the given radius. The x-coils are adjacent to one another and together span approximately 360° of arc. The same is true of the y-coils. The x-coils and y-coils are rotated 90° relative to one another, and the y-coils are positioned at a slightly greater radius than the x-coils, as discussed below.

The coil slots 61 and 63 were cut or otherwise formed in the 12.375-inch outer diameter coil form 57, 0.375 inch and 0.250 inch deep, respectively, for precisely positioning the axial sections of each x-coil 51 and each y-coil 53 at average radii $a_x=12.055$ inch and $a_y=12.180$ inch. The wire diameter is 0.109 inch. The x-coils are essentially identical to the y-coils except for their smaller radius and the 90° rotational displacement of their positions on the coil form 57.

Figures 9, 10:
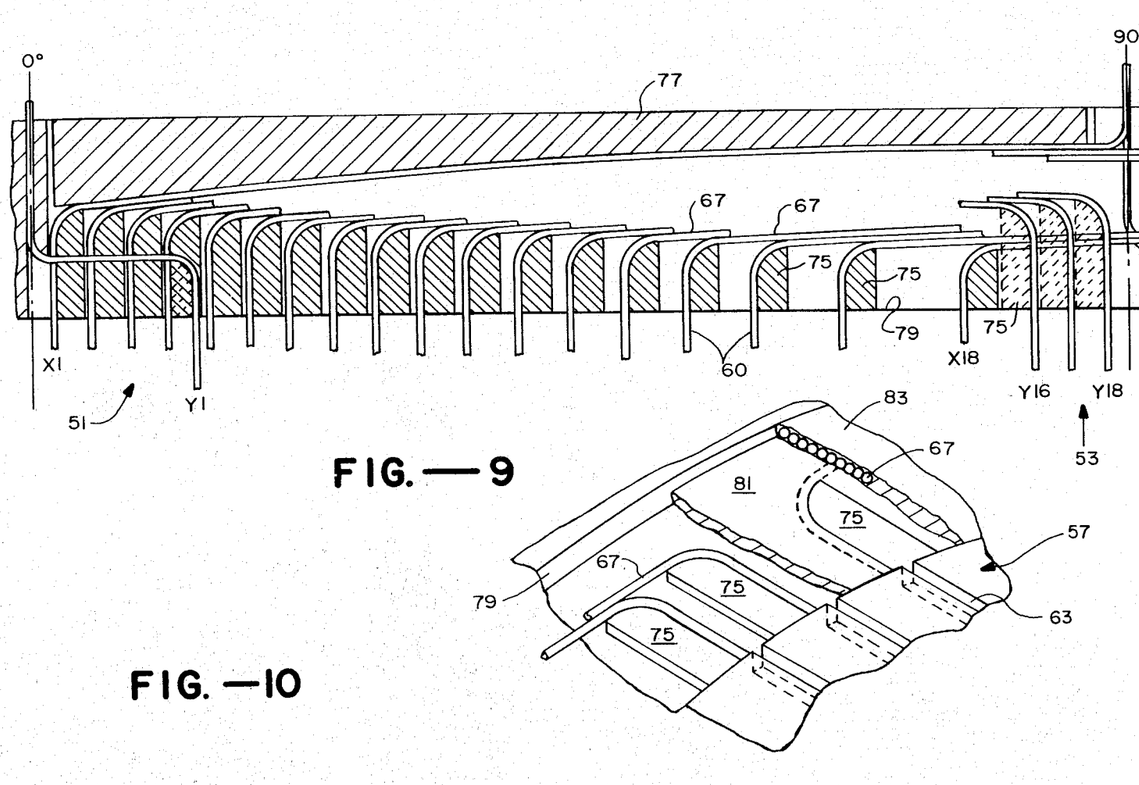
FIG. 9 is an enlarged view of a portion of FIG. 7, with the coil "unrolled" for clarity, and showing details of the coil end-mounting arrangement.
FIG. 10 is an enlarged view of a portion of FIG. 7 showing the spacers in the coil end-mounting arrangement.

As shown in FIG. 9, each of the coils was arranged in a continuous array of axial sections 60, individually designated X1–X36 (and X37–X72, Y19–Y54, Y5-5–Y18) which are substantially parallel to the cylinder axis 55 and which are joined by end connections or sections 67.

Figure 5:
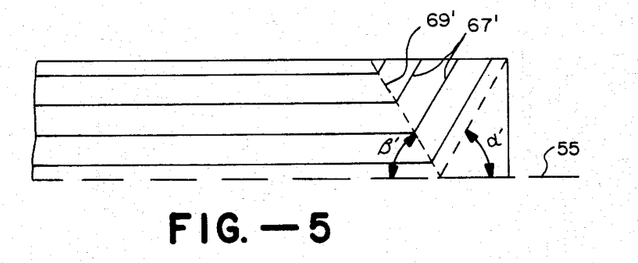
FIGS. 5 and 6 schematically illustrate, respectively in rolled (cylindrical) and unrolled coil configurations, the geometry and spacing of coil end connections which embody the present invention.
Figure 6:
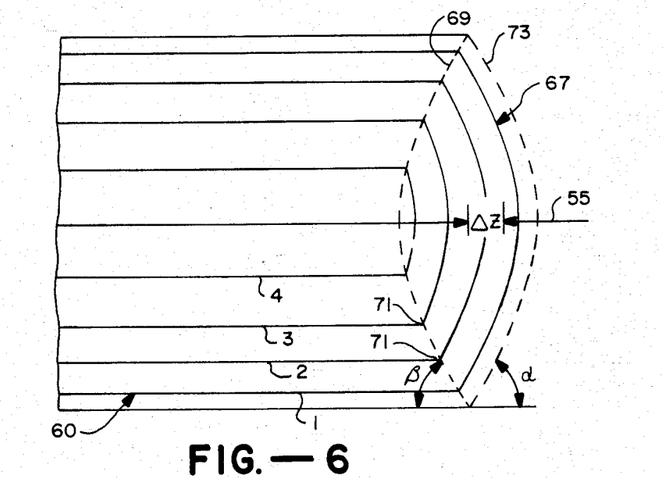

The geometric configuration of the coil end sections 67—67 are ideally designed so that the field distribution due to the end connections is described by the same harmonic spectrum as that due to the axial parts of the windings. In the case of an ideal continuous distribution of windings (finite dipole, all other multipoles equal zero) on the surface of a cylinder, a method for achieving this result is described in Mills and Morgan, "*A Flux Theorem for the Design of Magnet Coil Ends*", Particle Accelerators, 5, 227, 1973. This configuration, which may be adapted to any finite number of turns, is schematically shown in FIGS. 5 and 6 for four of the eighteen coil turns. As applied to the deflecting magnetic coil assembly 49, when the cylinder is unrolled as shown in FIG. 6, the curve 69 described by the intersections 71 of the end connections 67 with the respective axial coil sections 60 is symmetrical with respect to the individual end connections 67. Furthermore, each end connection 67 defines an angle, $\alpha$, relative to its axial coil section 60 which is substantially equal to the angle, $\beta$, thereto defined by the curve 69.

Viewed from the side as shown in the schematized partial plan view of FIG. 5, when the coil is positioned on the coil form 57, the curve 69 and end connections 67 are straight lines which define the equal angles $\alpha'$ and $\beta'$ which assume equal values for each intersection 71 and its associated end connection. It is assumed that for a sufficiently large number of turns, the ideal mathematical properties of this configuration are approximated with the same accuracy as the uniformity of the field due to the axial parts of the windings.

The above-described configuration and geometry are particularly well suited to all the equally-spaced-sine solutions ((b), (c) and (d)) for which the axial space available per turn, $\Delta z$ (FIG. 6), at the top of the cylinder is constant. In fact, if $\Delta z$ is made equal to the wire diameter so that all turns touch at the ends of the coil, the most compact solution of this type is obtained. The solution whose end connections lie exactly inside the ideal dashed lines is the equally spaced sine solution (b) discussed above. This solution, for which $\delta=0$, was therefore adopted using coils of 18 turns and a wire diameter $\Delta z$ of 0.109 inch. The solution is that illustrated in the drawing FIGS. 7, 9 and 10 with values of $\theta_t$ given by the first column of Table 2.

Referring now to FIGS. 9 and 10 as well as to FIG. 7, in an actual working embodiment of the coil assembly 49 the end connections 67—67 for the x-coils and y-coils were implemented by applying the x-coils to the form 57, using end connection spacers 75—75 of appropriate length and using retaining spacers 77—77, all of which were glued to the coil form's peripheral end section slot 79 (which, unlike the central coil form, itself contains no slots). The spacers 75—75 define the above-discussed predetermined configuration of the coil end sections 67—67. After the x-coil and associated spacers were affixed to the coil form, a coating 81 (FIG. 10) of liquid dielectric material such as epoxy resin was applied and cured to isolate the x-coils and provide a smooth base for the y-coils at the same level as the y-coil slots 63—63. Then, the appropriate sized end section spacers 75—75 and retaining spacers 77—77 were applied, followed by positioning of the y-coils, and application of another insulating layer 83 such as the above epoxy resin material. The coil assembly is thus ready for application of magnetic shield 59 described below, followed by a final insulative coating (not shown) of fiberglass tape or other suitable medium.

Referring to FIG. 7, the magnetic shield 59 of the present invention is a cylinder of inside radius R of high permeability material which is located on the outside of the coil form and serves three functions: (1) to shield the internal coil assembly region from external magnetic fields; (2) to increase and confine the field due to the windings; and (3) to equalize the effective radii of the x and y windings which are at different physical radii $a_x$ and $a_y$.

The radii equalization function of item (3) is thought to be novel; in constructing the magnetic shield 59 to specifications which satisfy this novel function, the shielding function and field-increasing and confining functions are thereby met.

In the past, magnet designs have achieved the necessary equal radii in different windings by spatially mixing the windings. According to the present invention, the magnetic shield 59 is located outside both coils and produces effective coil radii which are approximately equal, although the actual dimensions of the radii are different. Thus, one coil can be wound outside the other, thus simplifying construction considerably. This is the basis for the use, described previously, of the coil form 57 which has grooves therein for the y-coils and the x-coils, with the y-coils being wound outside the x-coils. The form 57 is amenable to forming grooves at precise locations to establish the angular location of the coil windings. In addition, the actual radii $a_x$ and $a_y$ of the coils are precisely defined and controlled by the coil form slots and the precisely-defined physical coil radii are then used in conjunction with the following design theory to provide equal effective radii, $a_{EFF}$.

Assuming that the condition of near infinite permeability of the shield material is met, if a coil is wound on a cylinder of radius a and the inside radius of the shield is R ($a<R$), the image currents of the coil currents are located at a radius $R^2/a$. The dipole field due to the coil currents plus image currents is then proportional to the quantity $[1+(a/R)^2]/a$. In terms of the difference in shield and coil radii, $\Delta R=a-R$, so that $a=R-\Delta R$ and the effective radius is $$a_{EFF} = R[1 - \tfrac{1}{4}(\Delta R/R)^2 + \ldots] \quad (11)$$

For coils which obey expression (11) the difference in the effective radii determied from the expression is negligible, i.e., it is much less than the actual difference in physical radii.

To illustrate, consider an actual working embodiment of the magnetic shield 59 and x- and y-coils of the present invention. In order to satisfy equation (11), the magnetic shield material was a very high permeability magnetic material such as that available under the tradename Moly Permalloy available from Allegheny Ludlum Steel, Corp., Pittsburgh, Pa. The dimensions of the shield were chosen so that its permeability was close to the maximum value for the Moly Permalloy, 300,000 to 500,000, a value sufficiently high for the expression (11) to be valid. The material comprised a tape 0.008 inches thick by 0.25 inch wide which was wound in 12 layers of overlapping helices, with the sense alternating with each layer, to reduce eddy currents. The inside shield radius R=12.375 inch and the values of $\Delta R_x$ and $\Delta R_y$ for the x- and y-coils were 0.320 inch and 0.195 inch. That is, the average coil radii were $a_y$=12.180 inch and $a_x$=12.055 inch. The percentage difference in the actual radii $a_x$ and $a_y$, given by $$\frac{a_y - a_x}{a_y},$$

was 1.03 percent. In contrast, the difference in the corresponding $a_{EFF}$ is determined by the difference in the bracket terms of equation (11), i.e., 0.99967–0.99988. Thus, the effective radii of the x and y coils differ by only 0.021 percent, despite the 1.03 percent difference in actual radii. In effect, the unique magnetic shielding technique has provided the required equal effective coil radii using a simplified construction technique which affords very precise definition of the coils and their associated radii.

Those of skill in the art will understand that the particular solutions described here for T=18 are dependent upon the dimensions of the deflecting coil, particularly the diameter of approximately 12 inches. Increasing (or decreasing) the diameter will possibly increase (decrease) the optimum number of turns in the associated best dipole solution. However, determination of the appropriate solution is exactly as described and will be readily attained. The solutions are, of course, unaffected by the axial length of the coil assembly 49.

We claim:

1. A magnet coil assembly for controllably deflecting an incident electron beam in an electron beam system such as a computed tomography scanner, comprising a pair of x- and y-coils and a generally cylindrical support form supporting the x-coil and the y-coil at physically different radii $a_x$ and $a_y$, the coils being at angular positions $\pi/2$ relative to one another and defining a generally cylindrical configuration about the axis thereof such that an angle $\phi$ defines the plane of deflection relative to a fixed plane containing the magnetic coil axis and polar coordinates (r, $\theta$) define the location in a plane defined by mutually orthogonal coordinate axes (x,y) normal to the magnetic coil axis; each coil comprising a selected number of continuous turns comprising a pair of generally axially-extending sections joined by end connecting sections; the direction and configuration of the coils being selected such that for currents $I_x$ proportional to $-\sin \phi$ and $I_y$ proportional to $\cos \phi$ producing magnetic fields $B_x$ equal to $-B_x \sin \phi$ and $B_y$ equal to $B_o \cos \phi$ then, to a selected accuracy, the magnitude of the resultant magnetic field approximates $$B_o = (B_x^2 + B_y^2)^{\frac{1}{2}},$$

which is a constant independent of R, $\theta$ and $\phi$, and the field direction $B_x/B_y$ approximates $$B_x/B_y = -\tan \phi,$$

independent of r and $\theta$;
wherein the selected accuracy is described by the following RMS errors for the case of a non-rotating field and for the case of a rotating field in the plane of deflection, the RMS error in the non-rotating case being (a) the square root of the mean square deviation of the magnetic field in any transverse plane from its value on axis, the average being taken over all polar angles ($\theta$) and over all radii (r') up to a selected radius (r), for each pair of coils separately, and the RMS error in the rotating case being (b) the square root of the mean square deviation of the magnetic field at any transverse plane, in the plane of deflection, from its value on axis, the average being taken over all values of the angle ($\phi$) defining the plane of deflection and over all radii (r') up to a selected radius (r) for the two pairs of coils acting together;

the angular positions $\theta_t$ of the axial sections of each coil being selected according to the formula $$\sin \theta_t = \frac{(2t-1)}{2T} + \delta,$$

where
t=1, 2, 3 . . . T,
T=the number of coil turns, and
in which for a given value of T the parameter $\delta$ is selected to provide a minimum value to at least one of (a) the root mean square error for the non-rotating case and (b) the root mean square error for the rotating case; or in which the parameters $\delta$ and T are selected to provide a value for at least one of said root mean square errors which is less than or equal to a predetermined percentage of the value of the magnetic field on the magnet axis; and further comprising a magnetic shield of high permeability material of radius R>$a_x$ and $a_y$ so that image currents of the coil currents are located at about $R^2/a$ for providing substantially equal effective radii for the x-coil and y-coil.

2. The deflecting magnet assembly of claim 1 in which the value of the parameter $\delta$ is selected to provide a value for both said root mean square errors which is less than or equal to 0.2 percent of the value of the magnetic field on the magnet axis.

3. The magnet coil assembly of claim 2 in which the value of the parameter $\delta$ is selected to provide a minimum value of the root mean square error for the non-rotating case, for T=18, r/a≈0.867.

4. The magnet coil assembly of claim 2 in which the value of the parameter $\delta$ is selected to provide a minimum value of the root mean square error for the rotating case, for T=18, r/a≈0.867.

5. The deflecting magnetic coil assembly of claim 1 wherein each end connection defines an angle relative to the extension of the respective axial section which is substantially equal to the angle relative thereto of a curve defined by a plurality of adjacent end connection intersections with respective axial sections.

6. The deflecting magnetic coil assembly of claim 5 wherein the curve described by the intersections of said end connections with the respective axial sections is symmetrical with respect to the individual end connections.

7. The deflecting magnetic coil assembly of claim 1 in which a compact configuration using $\delta=0$ is provided in which the intersection of the coil end connections with the coil axial sections define a first curve, each individual end connection defining a second curve symmetrical with and intersecting the corresponding section of the first curve and lying substantially inside a third curve which is symmetrical with the first curve and connected to the ends thereof.

8. The deflecting magnetic coil assembly of claims 1 or 7 wherein the value of the parameter T is 18 and the angular positions $\theta_t$ are defined by

| t = | $\theta_t \approx$ | |
|---|---|---|
| 1 | | 1.59° |
| 2 | | 4.78° |
| 3 | | 7.98° |
| 4 | | 11.21° |
| 5 | | 14.48° |
| 6 | | 17.79° |
| 7 | | 21.17° |
| 8 | | 24.62° |
| 9 | | 28.18° |
| 10 | | 31.86° |
| 11 | | 35.69° |
| 12 | | 39.71° |
| 13 | | 43.98° |
| 14 | | 48.59° |
| 15 | | 53.66° |
| 16 | | 59.44° |
| 17 | | 66.44° |
| 18 | | 76.46° |

9. The deflecting magnetic coil assembly of claim 7, in which the values of both said root mean square errors are less than 0.2 percent of the value of the magnetic field on the magnet axis.

10. The deflecting magnetic coil assembly of claim 8, in which the values of both said root mean square errors are less than 0.2 percent of the value of the magnetic field on the magnet axis.

* * * * *